(12) United States Patent
Cho et al.

(10) Patent No.: US 9,376,519 B2
(45) Date of Patent: Jun. 28, 2016

(54) TRANSITION METAL COMPOUND, CATALYTIC COMPOSITION INCLUDING THE SAME, AND METHOD FOR PREPARING POLYMER USING THE SAME

(71) Applicant: LG CHEM, LTD., Seoul (KR)

(72) Inventors: Yoonhee Cho, Daejeon (KR); Youngshil Do, Daejeon (KR); Yun Jin Lee, Daejeon (KR); A Rim Kim, Daejeon (KR); Choong Hoon Lee, Daejeon (KR); Seung Hwan Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/562,505

(22) Filed: Dec. 5, 2014

(65) Prior Publication Data

US 2015/0094435 A1    Apr. 2, 2015

Related U.S. Application Data

(63) Continuation of application No. PCT/KR2014/004643, filed on May 23, 2014.

(30) Foreign Application Priority Data

Sep. 26, 2013 (KR) ........................ 10-2013-0114253

(51) Int. Cl.
| | |
|---|---|
| C07F 17/00 | (2006.01) |
| C08F 4/6592 | (2006.01) |
| C08F 210/16 | (2006.01) |
| C08F 4/659 | (2006.01) |

(52) U.S. Cl.
CPC .............. *C08F 210/16* (2013.01); *C07F 17/00* (2013.01); *C08F 4/6592* (2013.01); *C08F 4/65908* (2013.01); *C08F 4/65912* (2013.01)

(58) Field of Classification Search
CPC .. C07F 17/00; C08F 6/65927; C08F 4/65908; C08F 4/65912; C08F 210/16
See application file for complete search history.

(56) References Cited

U.S. PATENT DOCUMENTS

| | | | |
|---|---|---|---|
| 5,064,802 A | 11/1991 | Stevens et al. | |
| 5,539,076 A | 7/1996 | Nowlin et al. | |
| 6,548,686 B2 | 4/2003 | Nabika et al. | |
| 6,576,723 B1 | 6/2003 | Bohnen et al. | |
| 7,504,354 B2 * | 3/2009 | Elder ................... | C07D 333/54 502/103 |
| 9,096,575 B2 | 8/2015 | Lee et al. | |
| 2005/0054791 A1 | 3/2005 | Nowlin et al. | |
| 2007/0225158 A1 | 9/2007 | Lee et al. | |
| 2010/0062927 A1 | 3/2010 | Lee et al. | |
| 2010/0087609 A1 | 4/2010 | Park et al. | |
| 2010/0093959 A1 | 4/2010 | Hong et al. | |
| 2010/0121006 A1 | 5/2010 | Cho et al. | |
| 2011/0152529 A1 | 6/2011 | Lee et al. | |
| 2011/0160413 A1 | 6/2011 | Lee et al. | |
| 2011/0172451 A1 | 7/2011 | Lee et al. | |
| 2011/0177935 A1 | 7/2011 | Lee et al. | |
| 2013/0203949 A1 | 8/2013 | Lee et al. | |
| 2013/0211020 A1 | 8/2013 | Lee et al. | |
| 2013/0211021 A1 | 8/2013 | Lee et al. | |
| 2013/0211023 A1 | 8/2013 | Lee | |
| 2013/0211024 A1 | 8/2013 | Lee et al. | |
| 2013/0296497 A1 | 11/2013 | Jeong et al. | |
| 2015/0011770 A1 | 1/2015 | Lee et al. | |

FOREIGN PATENT DOCUMENTS

| | | |
|---|---|---|
| CN | 1227570 A | 9/1999 |
| CN | 101213218 A | 7/2008 |
| CN | 102834402 A | 12/2012 |
| EP | 2873671 A1 | 5/2015 |
| JP | 2002-516358 A | 6/2002 |
| JP | 2003-201308 A | 7/2003 |
| JP | 2010-514836 A | 5/2010 |
| JP | 2010-526203 A | 7/2010 |
| JP | 2013-527271 A | 6/2013 |
| KR | 10-2001-0020425 A | 3/2001 |
| KR | 10-2005-0035183 A | 4/2005 |
| KR | 10-2007-0096465 A | 10/2007 |
| KR | 100820542 B1 | 4/2008 |
| KR | 10-2008-0049981 A | 6/2008 |
| KR | 10-2008-0065868 A | 7/2008 |
| KR | 10-2008-0097019 A | 11/2008 |
| KR | 10-2008-0101542 A | 11/2008 |
| KR | 10-0964093 B1 | 6/2010 |
| KR | 10-2010-0083076 A | 7/2010 |
| KR | 100986301 B1 | 10/2010 |
| KR | 10-2012-0024427 A | 3/2012 |
| KR | 10-1175338 B1 | 8/2012 |
| KR | 10-1299375 B1 | 8/2013 |
| WO | WO 2015/046930 A1 | 4/2015 |
| WO | WO 2015/046931 A1 | 4/2015 |
| WO | WO 2015/046932 A1 | 4/2015 |

OTHER PUBLICATIONS

Vernon C. Gibson et al., Advances in Non-Metallocene Olefin Polymerization Catalysis, Chemical Reviews, 2003, 103 (1), pp. 283-315.

You-Xian Chen et al., A Novel Phenolate "Constrained Geometry" Catalyst System. Efficient Synthesis, Structural Characterization, and a-Olefin Polymerization Catalysis, Organometallics, Dec. 23, 1997, vol. 16, Issue 26, pp. 5958-5963.

Yuetao Zhang et al., Constrained Geometry Tetramethylcyclopentadienyl-phenoxytitanium Dichlorides: Template Synthesis, Structures, and Catalytic Properties for Ethylene Polymerization, Organometallics, Feb. 2, 2004, vol. 23, Issue 3, pp. 540-546.

Steven D. R. Christie et al., Novel Routes to Bidentate Cyclopentadienyl-Alkoxide Complexes of Titanium: Synthesis of (η5-s-C5R14CHR2CH2CR3R4O)TiCl2, Organometallics, Feb. 1, 1999, vol. 18, Issue 3, pp. 348-359.

(Continued)

*Primary Examiner* — Caixia Lu

(74) *Attorney, Agent, or Firm* — Birch, Stewart, Kolasch & Birch, LLP

(57) ABSTRACT

The present specification describes a transition metal compound having a novel structure, a catalytic composition including the same, and a method for preparing a polymer using the same.

13 Claims, No Drawings

(56) References Cited

OTHER PUBLICATIONS

Alexander Rau et al., Synthesis and application in high-pressure polymerization of a titanium complex with a linked cyclopentadienyl-phenoxide ligand, Journal of Organometallic Chemistry, Aug. 25, 2000, vol. 608, Issues 1-2, pp. 71-75.

Esther E. C. G. Gielens, TitaniumHydrocarbyl Complexes with a LinkedCyclopentadienyl: Alkoxide AncillaryLigand; Participation of the Ligand in anUnusual Activation of a (Trimethylsilyl)methyl Group,Organometallics, Apr. 27, 1998, vol. 17,Issue 9, pp. 1652-1654.

Sung Hun Kim et al., Preparation of Thiophene-Fused and Tetrahydroquinoline-LinkedCyclopentadienyl Titanium Complexes for Ethylene/a-Olefin Copolymerization, Catalysts 2013(Feb. 6, 2013) 3, pp. 104-124.

Luke E. Turner et al., Facile resolution of constrained geometry indenyl-phenoxide ligation, Chemical Communications, 2003, pp. 1034-1035.

Extended European Search Report for European Application No. 14812388.8, dated Sep. 1, 2015.

Chinese Office Action for Appl. No. 201480001887.4 dated Feb. 23, 2016 (w/ English translation).

International Search Report (Form PCT/ISA/210) for International Application No. PCT/KR2014/008985, dated Dec. 26, 2014.

International Search Report (Form PCT/ISA/210) for International Application No. PCT/KR2014/008986, dated Dec. 23, 2014.

McDonagh et al., "Organometallic complexes for nonlinear optics Part 21. Syntheses and quadratic hyperpolarizabilities of alkynyl complexes containing optically active 1,2bis(methylphenylphosphino)-benzene ligands", Journal of Organometallic Chemistry, 2000, vol. 610, pp. 71-79.

Nayab et al., "Synthesis and characterization of novel tungsten complexes and their activity in the ROMP of cyclic olefins," Polyhedron, vol. 42, 2012 (Available online May 18, 2012), pp. 102-109.

* cited by examiner

TRANSITION METAL COMPOUND, CATALYTIC COMPOSITION INCLUDING THE SAME, AND METHOD FOR PREPARING POLYMER USING THE SAME

This application is a Continuation Bypass of International Application No. PCT/KR2014/004643, filed May 23, 2014, and claims the benefit of Korean Application No. 10-2013-0114253, filed on Sep. 26, 2013, all of which are hereby incorporated by reference in their entirety for all purposes as if fully set forth herein.

TECHNICAL FIELD

This application claims priority to and the benefits of Korean Patent Application No. 10-2013-0114253, filed with the Korean Intellectual Property Office on Sep. 26, 2013, the entire contents of which are incorporated herein by reference.

The present specification relates to a transition metal compound having a novel structure, a catalytic composition including the same, and a method for preparing a polymer using the same.

BACKGROUND ART

In early 1990s, Dow Corporation disclosed [Me$_2$Si(Me$_4$C$_5$)NtBu]TiCl$_2$ (Constrained-Geometry Catalyst, hereinafter abbreviated as CGC) in U.S. Pat. No. 5,064,802, and the superiority of CGC in a copolymerization reaction of ethylene and alpha-olefin compared to existing metallocene catalysts known in the art is mainly summarized into two points as follows: (1) a polymer having a high molecular weight while exhibiting high activity even at a high polymerization temperature is produced, and (2) copolymerizability of alpha-olefin having high steric hindrance such as 1-hexene and 1-octene is highly superior. In addition to these, various properties of CGC have been gradually known in polymerization reactions, and as a result, efforts to synthesize derivatives of CGC to use these as a polymerization catalyst have been actively made in both academics and industries.

As one approach among these efforts, synthesis of metal compounds in which other various bridges and nitrogen substituents are introduced instead of a silicon bridge, and polymerization of these metal compounds have been tried. The representative metal compounds that have been known till recently are the following Compounds (1) to (4) (Chem. Rev. 2003, 103, 283).

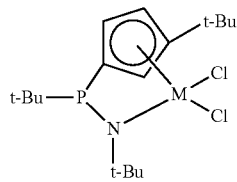

(1)

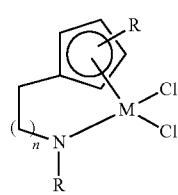

(2)

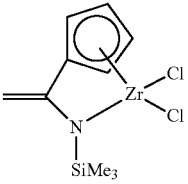

(3)

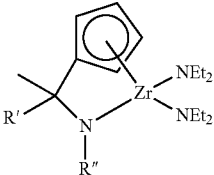

(4)

In Compounds (1) to (4), phosphorous (1), ethylene or propylene (2), methylidene (3), and methylene (4) bridges are introduced, respectively, instead of a silicon bridge having a CGC structure, however, improved results compared to CGC have not been obtained in terms of activity or copolymerization efficiency when used in ethylene polymerization or copolymerization with alpha-olefin.

Furthermore, as another approach, compounds formed with oxido ligands instead of amido ligands of CGC have been actively synthesized, and polymerization using these compounds also haven been partly tried. Examples thereof are summarized as follows.

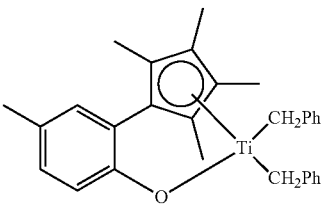

(5)

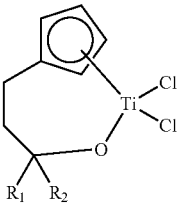

(6)

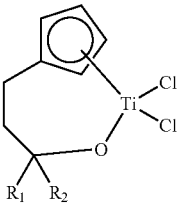

(7)

-continued (8)

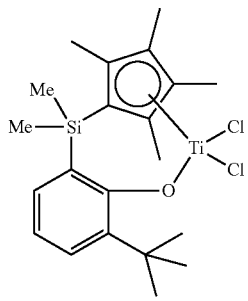

Compound (5) was reported by T. J. Marks et al. and in the compound, a cyclopentadiene (Cp) derivative and an oxido ligand are cross-linked by an ortho-phenylene group (Organometallics 1997, 16, 5958). Compounds having the same cross-linking and polymerization using these were also reported by Mu et al. (Organometallics 2004, 23, 540). In addition, the indenyl ligand and the oxido ligand being cross-linked by the same ortho-phenylene group was reported by Rothwell et al. (Chem. Commun. 2003, 1034). Compound (6) was reported by Whitby et al., and in the compound, a cyclopentadienyl ligand and an oxide ligand are crossed by 3 carbons (Organometallics 1999, 18, 348), and these catalysts were reported to exhibit activities for syndiotactic polystyrene polymerization. Similar compounds were also reported by Hessen et al. (Organometallics 1998, 17, 1652). Compound (7) was reported by Rau et al., and the compound shows an activity for ethylene polymerization and ethylene/1-hexene copolymerization at a high temperature and high pressure (210° C., 150 mPa) (J. Organomet. Chem. 2000, 608, 71). After that, synthesis of catalysts having similar structures (8) and high-temperature and high-pressure polymerization using these catalysts were applied for a patent by Sumitomo Corporation (U.S. Pat. No. 6,548,686). However, among the attempts described above, only a small number of catalysts are practically used in commercial plants. Accordingly, catalysts showing more improved comprehensive performances have been required, and simple methods for preparing these catalysts have been required as well.

PRIOR ART DOCUMENTS

Patent Documents

U.S. Pat. No. 5,064,802
U.S. Pat. No. 6,548,686

Non-Patent Documents

Chem. Rev. 2003, 103, 283
Organometallics 1997, 16, 5958
Organometallics 2004, 23, 540
Chem. Commun. 2003, 1034
Organometallics 1999, 18, 348
Organometallics 1998, 17, 1652
J. Organomet. Chem. 2000, 608, 71

DISCLOSURE

Technical Problem

The present specification describes a transition metal compound having a novel structure, a catalytic composition including the same, and a method for preparing a polymer using the same.

Technical Solution

One embodiment of the present specification provides a transition metal compound of the following Chemical Formula 1.

[Chemical Formula 1]

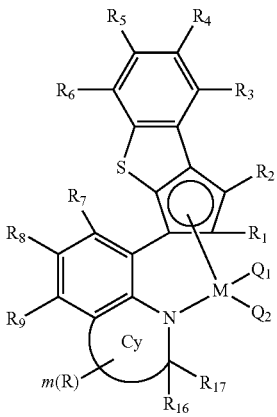

In Chemical Formula 1,

M is a group 4 transition metal, $Q_1$ and $Q_2$ are the same as or different from each other, and each independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms, $R_1$ to $R_6$ are the same as or different from each other, and each independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of group 14 metal substituted with hydrocarbyl having 1 to 20 carbon atoms; and $R_1$ and $R_2$ may bond to each other, or 2 or more of $R_3$ to $R_6$ may bond to each other to form an aliphatic ring having 5 to 20 carbon atoms or an aromatic ring having 6 to 20 carbon atoms; and the aliphatic ring or the aromatic ring may be substituted with halogen, alkyl having 1 to 20 carbon atoms, alkenyl having 2 to 20 carbon atoms, or aryl having 6 to 20 carbon atoms, $R_7$ to $R_9$ are the same as or different from each other, and each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; and at least two of $R_7$ to $R_9$ may bond to each other to form an aliphatic ring having 5 to 20 carbon atoms or an aromatic ring having 6 to 20 carbon atoms; and the aliphatic ring or the aromatic ring may be substituted with halogen, alkyl having 1 to 20 carbon atoms, alkenyl having 2 to 20 carbon atoms, or aryl having 6 to 20 carbon atoms, Cy is a 5-membered or 6-membered aliphatic ring, R, $R_{16}$ and $R_{17}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; and m is an integer of 0 to 2 when Cy is a 5-membered aliphatic ring, and an integer of 0 to 4 when Cy is a 6-membered aliphatic ring.

Another embodiment of the present specification provides a catalytic composition including the transition metal compound of Chemical Formula 1.

Still another embodiment of the present specification provides a method for preparing a polymer using the catalytic composition.

Advantageous Effects

In a transition metal compound according to the present invention, the metal site surroundings have a solid pentagonal ring structure by an amido group linked to a phenylene bridge thereby are stably maintained, and as a result, approaches of monomers are structurally very convenient, and the transition metal compound has a structure fused with a thiophene structure fused with a benzene ring. Consequently, polymers having a narrower MWD compared to CGC, having excellent copolymerizability and having a high molecular weight in a low density area can be prepared by using a catalytic composition including the transition metal compound.

MODE FOR DISCLOSURE

According to one embodiment of the present invention, a transition metal compound of Chemical Formula 1 described above is provided.

In the transition metal compound of Chemical Formula 1 described in the present specification, the metal site is linked by a cyclopentadienyl ligand in which an amido group linking to a phenylene bridge in a ring form is introduced, therefore, structurally, the Cp-M-N angle is small, and the Q1-M-Q2 angle approached by a monomer is maintained to be wide. In addition, in the structure of the compound represented by Chemical Formula 1, the benzothiophene-fused cyclopentadiene, the phenylene bridge, the nitrogen and the metal site are consecutively linked in a ring form, therefore, a more stable and solid pentagonal ring structure is formed, which is different from a CGC structure linked by a silicon bridge. Therefore, these compounds may produce polyolefin having a high activity, high molecular weight and high copolymerizability even at a high polymerization temperature when used for olefin polymerization after these compounds are reacted with cocatalysts such as methylaluminoxane or $B(C_6F_5)_3$ and activated. Particularly, very low-density copolymers having density of less than 0.910 g/cc may also be prepared since, due to the structural characteristics of the catalyst, large amounts of alpha-olefin may be introduced as well as linear low-density polyethylene having a density level of 0.910 to 0.930 g/cc. Particularly, polymers having a narrower MWD compared to CGC, having excellent copolymerizability and having a high molecular weight in a low density area may be prepared by using a catalytic composition including the transition metal compound. In addition, various substituents may be introduced to benzothiophene-fused cyclopentadienyl and quinolone-based compounds, and ultimately, structures and properties of the produced polyolefin may be adjusted by readily controlling the electronic and steric environments around the metal. The compound of Chemical Formula 1 is preferably used to prepare a catalyst for the polymerization of olefin monomers, but the application is not limited thereto, and the compound may be applied to all other fields in which the transition metal compound may be used.

In the present specification, the alkyl and the alkenyl may be each linear or branched.

In the present specification, the silyl may be silyl substituted with alkyl having 1 to 20 carbon atoms, and examples thereof include trimethylsilyl or triethylsilyl.

In the present specification, the aryl includes monocyclic or multicyclic aryl, and specific examples thereof include phenyl, naphthyl, anthryl, phenanthryl, crycenyl, pyrenyl and the like.

According to another embodiment of the present specification, Chemical Formula 1 may be represented by the following Chemical Formula 2 or 3.

[Chemical Formula 2]

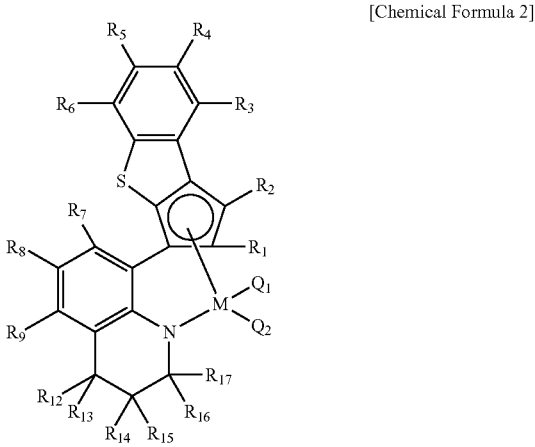

In Chemical Formula 2, $R_{12}$ to $R_{17}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the rest of the substituents are the same as those in Chemical Formula 1.

[Chemical Formula 3]

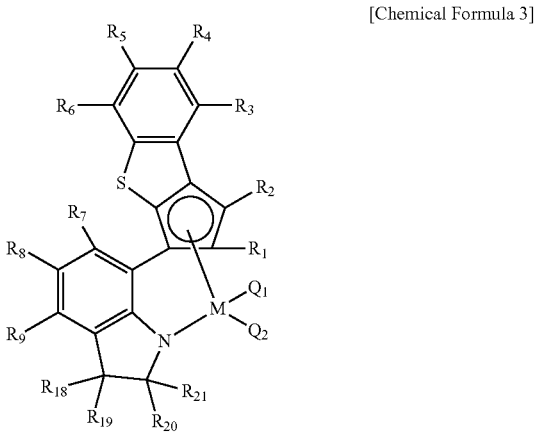

In Chemical Formula 3, $R_{18}$ to $R_{21}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the rest of the substituents are the same as those in Chemical Formula 1.

According to another embodiment of the present specification, $R_1$ and $R_2$ are alkyl having 1 to 20 carbon atoms.

According to another embodiment of the present specification, $R_1$ and $R_2$ are alkyl having 1 to 6 carbon atoms.

According to another embodiment of the present specification, $R_1$ and $R_2$ are methyl.

According to another embodiment of the present specification, $R_3$ to $R_6$ are the same as or different from each other, and each independently hydrogen; alkyl having 1 to 20 carbon atoms; or alkenyl having 2 to 20 carbon atoms.

According to another embodiment of the present specification, $R_3$ to $R_6$ are the same as or different from each other, and each independently hydrogen; or alkyl having 1 to 20 carbon atoms.

According to another embodiment of the present specification, $R_3$ to $R_6$ are the same as or different from each other, and each independently hydrogen.

According to another embodiment of the present specification, $R_{12}$ to $R_{17}$ of Chemical Formula 2 are each independently hydrogen; alkyl having 1 to 20 carbon atoms; or alkenyl having 2 to 20 carbon atoms.

According to another embodiment of the present specification, $R_{12}$ to $R_{17}$ of Chemical Formula 2 are each independently hydrogen; or alkyl having 1 to 20 carbon atoms.

According to another embodiment of the present specification, $R_{12}$ to $R_{17}$ of Chemical Formula 2 are hydrogen.

According to another embodiment of the present specification, $R_{12}$ to $R_{16}$ of Chemical Formula 2 are hydrogen, and $R_{17}$ is alkyl having 1 to 20 carbon atoms.

According to another embodiment of the present specification, $R_{12}$ to $R_{16}$ of Chemical Formula 2 are hydrogen, and $R_{17}$ is methyl.

According to another embodiment of the present specification, $R_{18}$ to $R_{21}$ of Chemical Formula 3 are each independently hydrogen; alkyl having 1 to 20 carbon atoms; or alkenyl having 2 to 20 carbon atoms.

According to another embodiment of the present specification, $R_{18}$ to $R_{21}$ of Chemical Formula 3 are each independently hydrogen; or alkyl having 1 to 20 carbon atoms.

According to another embodiment of the present specification, $R_{18}$ to $R_{21}$ of Chemical Formula 3 are hydrogen.

According to another embodiment of the present specification, $R_{18}$ to $R_{20}$ of Chemical Formula 3 are hydrogen, and $R_{21}$ is alkyl having 1 to 20 carbon atoms.

According to another embodiment of the present specification, $R_{18}$ to $R_{20}$ of Chemical Formula 3 are hydrogen, and $R_{21}$ is methyl.

According to another embodiment of the present specification, M is Ti, Hf or Zr.

In the present specification, the transition metal compound represented by Chemical Formula 1 may be represented by any one of the following chemical formulae, but is not limited thereto.

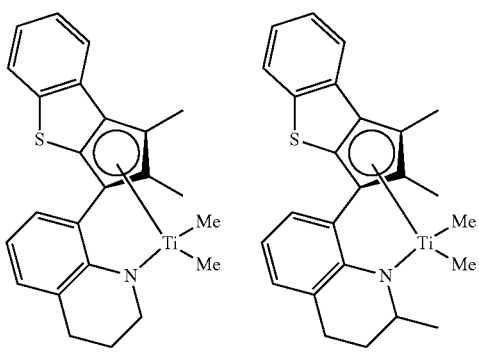

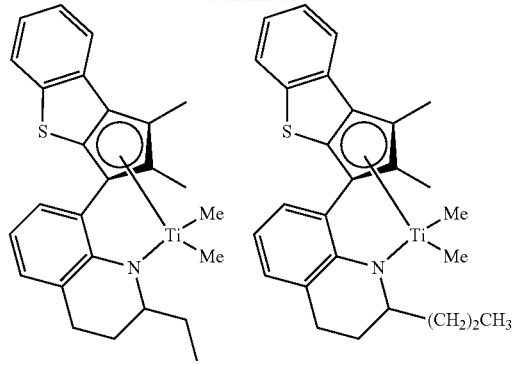

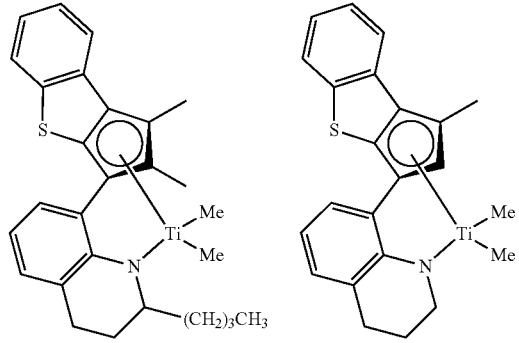

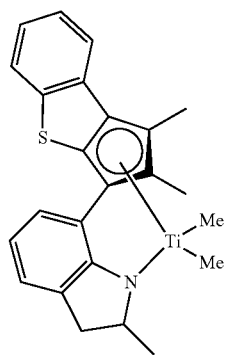

The compound of Chemical Formula 1 may be prepared by the following Steps a) to d):

a) a step of preparing a compound represented by the following <Chemical Formula 6> by reacting an amine-based compound represented by the following <Chemical Formula 5> and alkyllithium, and then adding a compound including a protecting group (—$R_0$,) thereto;

b) a step of preparing an amine-based compound represented by the following <Chemical Formula 8> by reacting the compound represented by <Chemical Formula 6> and alkyllithium, and then adding a ketone-based compound represented by the following <Chemical Formula 7> thereto;

c) a step of preparing a dilithium compound represented by the following <Chemical Formula 9> by reacting the compound represented by <Chemical Formula 8> and n-butyllithium; and d) a step of preparing the transition metal compound represented by Chemical Formula 1 by reacting the compound represented by <Chemical Formula 9>, $MCl_4$ (M=group 4 transition metal) and an organic lithium compound.

[Chemical Formula 5]

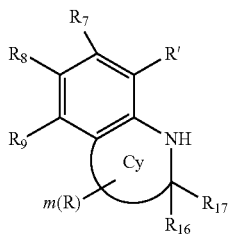

[Chemical Formula 6]

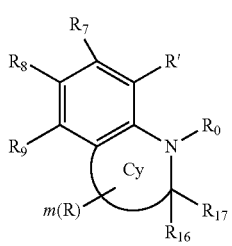

[Chemical Formula 7]

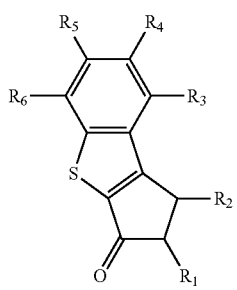

[Chemical Formula 8]

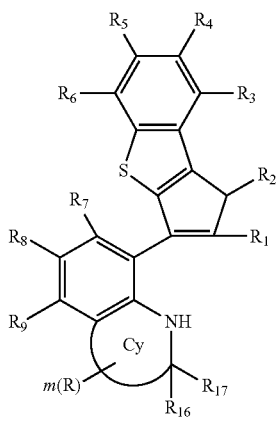

[Chemical Formula 9]

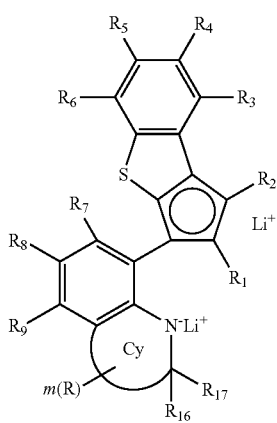

In Chemical Formulae 5 to 9,
R' is hydrogen,
$R_0$ is a protecting group, and other substituents are the same as those defined in Chemical Formula 1.

In step a), the compound including a protecting group may be selected from among trimethylsilyl chloride, benzyl chloride, t-butoxycarbonyl chloride, benzyloxycarbonyl chloride, carbon dioxide and the like.

When the compound including a protecting group is carbon dioxide, Chemical Formula 6 may be a lithium carbamate compound represented by the following Chemical Formula 6a.

[Chemical Formula 6a]

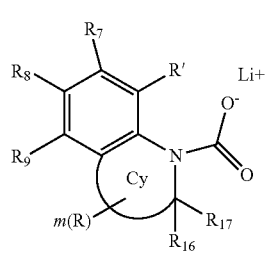

The descriptions on the substituents are the same as those in Chemical Formula 6.

According to one specific embodiment, the compound of Chemical Formula 1 may be prepared by the following Reaction Formula 1.

[Reaction Formula 1]

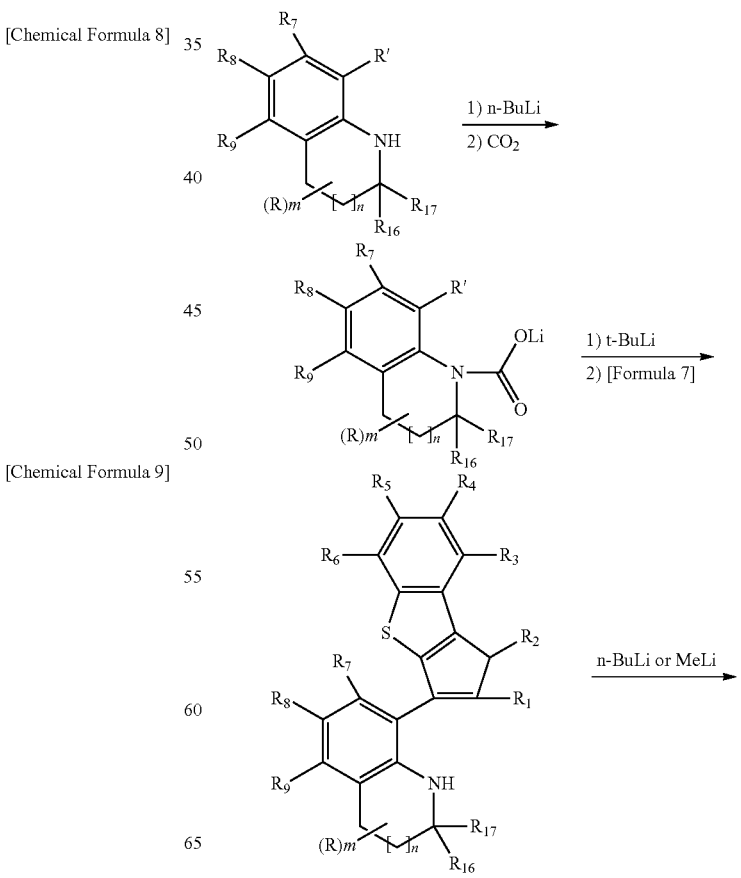

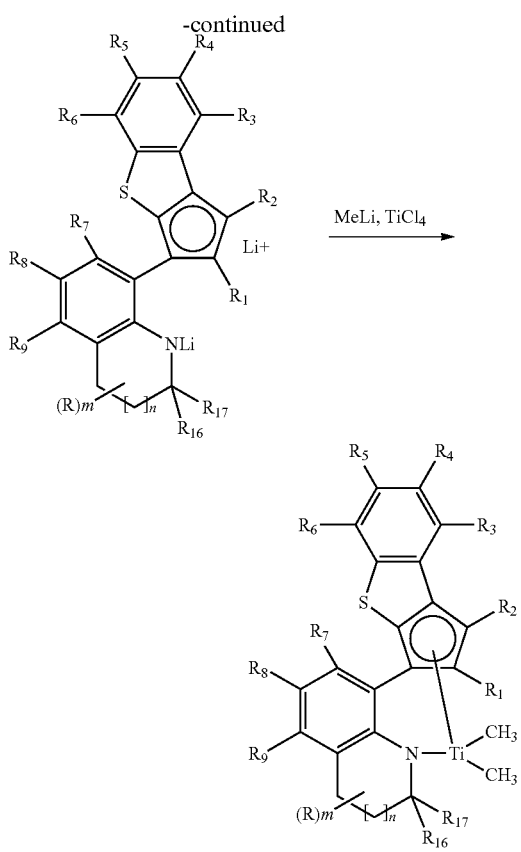

In Reaction Formula 1, the descriptions on the substituents are the same as those in Chemical Formula 1, and n is 0 or 1.

The present specification also provides a catalytic composition including the compound of Chemical Formula 1.

The catalytic composition may further include a cocatalyst. As the cocatalyst, cocatalysts known in the art may be used.

For example, the catalytic composition may further include at least one of the following Chemical Formulae 10 to 12 as a cocatalyst.

[Al($R_{22}$)—O]$_a$—      [Chemical Formula 10]

In the above formula, $R_{22}$s are each independently a halogen radical; a hydrocarbyl radical having 1 to 20 carbon atoms; or a hydrocarbyl radical having 1 to 20 carbon atoms substituted with halogen; and a is an integer of 2 or greater;

D($R_{22}$)$_3$      [Chemical Formula 11]

in the above formula, D is aluminum or boron; and $R_{22}$s are each independently the same as those defined above; and

[L-H]$^+$[Z(A)$_4$]$^-$ or [L]$^+$[Z(A)$_4$]$^-$      [Chemical Formula 12]

in the above formula, L is a neutral or cationic Lewis acid; H is a hydrogen atom; Z is a group 13 element; As are each independently aryl having 6 to 20 carbon atoms or alkyl having 1 to 20 carbon atoms in which one or more hydrogen atoms may be substituted with substituents; and the substituents are halogen, hydrocarbyl having 1 to 20 carbon atoms, alkoxy having 1 to 20 carbon atoms, or aryloxy having 6 to 20 carbon atoms.

As a method for preparing the catalytic composition, a first preparation method including the steps of obtaining a mixture by bringing the transition metal compound represented by Chemical Formula 1 in contact with the compound represented by Chemical Formula 10 or Chemical Formula 11; and adding the compound represented by Chemical Formula 12 thereto is provided.

A second method for preparing a catalytic composition is provided by bringing the transition metal compound represented by Chemical Formula 1 in contact with the compound represented by Chemical Formula 12.

In the first method of the methods preparing the catalytic composition, the molar ratio of the compound represented by Chemical Formula 10 or Chemical Formula 11 with respect to the transition metal compound of Chemical Formula 1 preferably ranges from 1:2 to 1:5,000, more preferably 1:10 to 1:1,000, and most preferably 1:20 to 1:500.

Meanwhile, the molar ratio of the compound represented by Chemical Formula 12 with respect to the transition metal compound of Chemical Formula 1 preferably ranges from 1:1 to 1:25, more preferably 1:1 to 1:10, and most preferably 1:1 to 1:5.

When the molar ratio of the compound represented by Chemical Formula 10 or Chemical Formula 11 with respect to the transition metal compound of Chemical Formula 1 is less than 1:2, there is a problem in that the alkylation of the metal compound is not completely progressed since the amount of the alkylating agent is very small, and when the molar ratio is greater than 1:5,000, the alkylation of the metal compound is achieved, however, there is a problem in that the activation of the alkylated metal compound is not completely achieved due to the side reaction between the remaining excess alkylating agent and the activating agent of Chemical Formula 12. In addition, when the molar ratio of the compound represented by Chemical Formula 12 with respect to the transition metal compound of Chemical Formula 1 is less than 1:1, there is a problem in that the activity of the produced catalytic composition decreases since the amount of the activating agent is relatively small and the activation of the metal compound is not completely achieved, and when the molar ratio is greater than 1:25, the activation of the metal compound is completely achieved, however, there is a problem in that the unit cost of the catalytic composition is not economical due to the remaining excess activating agent or the purity of the produced polymer decreases.

In the second method of the methods preparing the catalytic composition, the molar ratio of the compound represented by Chemical Formula 12 with respect to the transition metal compound of Chemical Formula 1 preferably ranges from 1:1 to 1:500, more preferably 1:1 to 1:50, and most preferably 1:2 to 1:25. When the molar ratio is less than 1:1, there is a problem in that the activity of the produced catalytic composition decreases since the amount of the activating agent is relatively small and the activation of the metal compound is not completely achieved, and when the molar ratio is greater than 1:500, the activation of the metal compound is completely achieved, however, there is a problem in that the unit cost of the catalytic composition is not economical due to the remaining excess activating agent or the purity of the produced polymer decreases.

As the reaction solvent used in the preparation of the composition, a hydrocarbon-based solvent such as pentane, hexane and heptane, or an aromatic-based solvent such as benzene and toluene may be used, but the solvent is not limited thereto and all solvents capable of being used in the art may be used.

In addition, the transition metal compound of Chemical Formula 1 and a cocatalyst may be used in a carrier-supported form. As the carrier, silica or alumina may be used.

The compound represented by Chemical Formula 10 is not particularly limited as long as the compound is alkylaluminoxane. Preferable examples thereof include methylaluminoxane, ethylaluminoxane, isobutylaluminoxane, butylaluminoxane and the like, and a particularly preferable compound is methylaluminoxane.

The compound represented by Chemical Formula 11 is not particularly limited, however, preferable examples thereof include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron and the like, and particularly preferable compounds are selected from among trimethylaluminum, triethylaluminum and triisobutylaluminum.

Examples of the compound represented by Chemical Formula 12 include triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium, tetraphenylboron, N,N-diethylanilinium tetraphenylboron, N,N-diethylanilinium tetra pentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentatetraphenylaluminum, triphenylphosphonium tetraphenylaluminum, trimethylphosphonium tetraphenylaluminum, triethylammonium tetraphenylaluminum, tributylammonium tetraphenylaluminum, trimethylammonium tetraphenylboron, tripropylammonium tetraphenylboron, trimethylammonium tetra(p-tolyl)boron, tripropylammonium tetra(p-tolyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, triphenylcarbonium tetra(p-trifluoromethylphenyl)boron, triphenylcarbonium tetrapentafluorophenylboron and the like.

A polyolefin homopolymer or copolymer may be prepared by bringing the catalytic composition including one or more compounds selected from among the transition metal compound of Chemical Formula 1; and the compounds represented by Chemical Formula 10 to Chemical Formula 12 in contact with one or more olefin monomers.

The most preferable preparation process using the catalytic composition is a solution process, and a slurry or a vapor process may also be used when this composition is used with an inorganic carrier such as silica.

In the preparation process, the activated catalytic composition may be injected by dissolving in or diluted with aliphatic hydrocarbon solvents having 5 to 12 carbon atoms such as pentane, hexane, heptane, nonane, decane and isomers thereof, aromatic hydrocarbon solvents such as toluene and benzene, and hydrocarbon solvents substituted with a chlorine atom such as dichloromethane and chlorobenzene, which are suitable for olefin polymerization processes. In the solvent used herein, a small amount of water, air or the like, which act as a catalytic poison, is preferably removed by being treated with a small amount of alkylaluminum, or cocatalysts may also be further used.

Examples of the olefin-based monomers capable of being polymerized with the metal compounds using a cocatalyst include ethylene, alpha-olefin, cyclic olefin and the like, and diene olefin-based monomers or triene olefin-based monomers having two or more double bonds may also be polymerized. Specific examples of the monomers include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbonene, norbonadiene, ethylidene norbonene, phenyl norbonene, vinyl norbonene, dicyclopentadiene, 1,4-butadiene, 1,5-pentadiene, 1,6-hexadiene, styrene, alpha-methylstyrene, divinylbenzene, 3-chloromethylstyrene and the like, and copolymerization may also be carried out by mixing two or more types of these monomers.

In particular, in the preparation method of the present invention, a very low-density copolymer having a high molecular weight and a polymer density of 0.91 g/cc or less may be prepared using the catalytic composition in a copolymerization reaction of monomers having high steric hindrance such as ethylene and 1-octene even at a high reaction temperature of 90° C. or higher.

According to one embodiment, the polymer prepared using the preparation method of the present invention has density of less than 0.91 g/cc.

According to another embodiment, the polymer prepared using the preparation method of the present invention has density of less than 0.89 g/cc.

According to one embodiment, the polymer prepared using the preparation method of the present invention has density of 0.885 g/cc or less.

According to one embodiment, the polymer prepared using the preparation method of the present invention has a Tc of 75 or less.

According to one embodiment, the polymer prepared using the preparation method of the present invention has a Tm of 95 or less.

According to one embodiment, the polymer prepared using the preparation method of the present invention has a Tm of 91 or less.

According to one embodiment, the polymer prepared using the preparation method of the present invention has a Tm of less than 87.

According to one embodiment, the polymer prepared using the preparation method of the present invention has an Mw of 100,000 or greater.

According to another embodiment, the polymer prepared using the preparation method of the present invention has an Mw ranging from 100,000 to 1,000,000.

According to one embodiment, the polymer prepared using the preparation method of the present invention has an MWD of 3 or less.

According to another embodiment, the polymer prepared using the preparation method of the present invention has an MWD ranging from 1 to 3.

According to another embodiment, the polymer prepared using the preparation method of the present invention has an MWD ranging from 1.5 to 2.9.

According to another embodiment, the polymer prepared using the preparation method of the present invention has an MWD ranging from 2 to 2.85.

According to one embodiment, the polymer according to the present invention has an MWD ranging from 1 to 3, an Mw ranging from 100,000 to 1,000,000, and density of less than 0.91 g/cc.

Hereinafter, the present invention will be described in more detail with reference to examples shown below. However, these examples are for illustrative purposes only, and the scope of the present invention is not limited thereto.

Synthesis of Ligand and Transition Metal Compound

Unless otherwise specified, organic reagents and solvents were purchased from Aldrich. Co., purified using standard methods, and used. The reproducibility of the experiments was enhanced by blocking the contact with air and moisture in all steps of the syntheses. The compound in which R1 to R6 are methyl among the ketone-based compounds in Chemical Formula 7 was synthesized using the method published in the literature [*Organometallics* 2002, 21, 2842-2855], CGC (Me$_2$Si(Me$_4$C$_5$)NtBu]TiMe$_2$ (Constrained-Geometry Catalyst, hereinafter abbreviated as CGC) of Comparative Example 1 was synthesized using the method disclosed in U.S. Pat. No. 6,015,916, and Compound A of Comparative Example 2 was synthesized using the method published in the literature [*Dalton Trans.*, 2010, 39, 9994-10002].

Synthesis of Compound 1

Preparation of 8-(1,2-dimethyl-3H-benzo(b)cyclopenta(d)thiophen-3-yl)-1,2,3,4-tetrahydroquinoline compound 1,2,3,4-tetrahydroquinoline (2 g, 2.25 mmol) and diethylether (50 ml) were placed in a Schlenk flask. The Schlenk flask was immersed in a low temperature bath of −78° C. made of dry ice and acetone, and the mixture in the flask was stirred for 30 minutes. Subsequently, n-butyllithium (n-BuLi, 9.8 ml, 2.5 M, 24.6 mmol) was injected with a syringe under argon atmosphere, and light yellow slurry was formed. Next, the result in the flask was stirred for 17 hours, and then the temperature of the flask was raised to room temperature while removing the generated butane gas. The temperature was lowered by immersing the flask in a low temperature bath of −78° C. once again, and CO$_2$ gas was introduced thereto. As the carbon dioxide gas was introduced, the slurry disappeared and the result became a transparent solution. The temperature was raised to room temperature as the carbon dioxide was removed by connecting the flask to a bubbler. After that, extra CO$_2$ gas and the solvent were removed under vacuum. After the flask was transferred to a dry box, pentane was added thereto and the result was stirred vigorously to obtain lithium carbamate as a white solid compound. The white solid compound is coordinate bonded to diethylether. The yield was 100%.

$^1$H NMR (C$_6$D$_6$, C$_5$D$_5$N): δ 1.90 (t, J=7.2 Hz, 6H, ether), 1.50 (br s, 2H, quin-CH$_2$, 2.34 (br s, 2H, quin-CH$_2$), 3.25 (q, J=7.2 Hz, 4H, ether), 3.87 (br, s, 2H, quin-CH$_2$), 6.76 (br d, J=5.6 Hz, 1H, quin-CH) ppm, $^{13}$C NMR (C$_6$D$_6$): δ 24.24, 28.54, 45.37, 65.95, 121.17, 125.34, 125.57, 142.04, 163.09 (0=0) ppm.

The lithium carbamate compound (3.91 g, 21.36 mmol) prepared above was placed in a Schlenk flask. Subsequently, tetrahydrofuran (2 g, 27.77 mmol) and 45 ml of diethylether were added thereto in consecutive order. After the Schlenk flask was immersed in a low temperature bath of −20° C. made of acetone and a small amount of dry ice, the mixture in the flask was stirred for 30 minutes, and tert-BuLi (17 ml, 28.84 mmol) was added thereto. At this moment, the color of the reaction mixture turned to red. The result was stirred for 3 hours while maintaining the temperature at −20° C. Lithium bromide (LiBr) (3.15 g, 36.3 mmol) and 1,2-dimethyl-1H-benzo(b)cyclopenta(d)thiophen-3(2H)-one (3 g, 13.88 mmol) dissolved in 15 ml of tetrahydrofuran were mixed in a syringe, and the mixture was injected to the flask under argon atmosphere. The result was reacted for 17 hours while maintaining the temperature at −20° C., and then the constant temperature bath was removed and the temperature was maintained at room temperature. Subsequently, water (15 ml) was added to the flask, then dimethyl chloride was added thereto, and the result was transferred to a separatory funnel. Hydrochloric acid (3N, 50 ml) was added thereto and the result was shaken for 12 minutes. Next, the result was neutralized by adding a saturated aqueous sodium bicarbonate solution (100 ml), and then the organic layer was extracted. Anhydrous magnesium sulfate was added to this organic layer in order to remove moisture, the result was filtered, the filtrate was collected, and the solvent was removed. The obtained filtrate was purified by a column chromatography method using a hexane and dimethyl chloride (v/v, 10:1) solvent to obtain yellow solids. The yield was 57.15%.

$^1$H NMR (C$_6$D$_6$, C$_5$D$_5$N): δ 1.22 (t, J=8.5 Hz, 3H, Cp-CH$_3$), 1.61 (m, 2H, quin-CH$_2$), 1.88 (s, 3H, Cp-CH$_3$), 2.59 (br d, J=5.5 Hz, 2H, quin-CH$_2$), 2.87 (br s, 2H, quin-CH$_2$), 3.12 (m, 1H, Cp-H), 3.81 (br d, J=25 Hz, 1H, N—H), 6.76 (m, J=7 Hz, 1H, ph-CH), 6.95 (d, J=7 Hz, 1H, ph-CH), 7.02 (t, J=7.5 Hz, 1H, quin-CH), 7.25 (m, 2H), 7.55 (d, J=8 Hz, 1H, quin-CH), 7.63 (t, J=9.5 Hz, 1H, ph-CH) ppm.

Preparation of [8-(1,2-dimethyl-3H-benzo(b)cyclopenta(d)thiophen-3-yl)-1,2,3,4-tetrahydroquinoline] titanium dimethyl compound After the 8-(1,2-dimethyl-3H-benzo(b)cyclopenta(d)thiophen-3-yl)-1,2,3,4-tetrahydroquinoline (1 g, 3.02 mmol) prepared in Example 1 and 30 ml of diethylether were placed in a round-bottom flask in a dry box, the temperature was lowered to −30° C., and MeLi (11.3 ml, 1.6 M, 18.1 mmol) was slowly added while stirring. The mixture was reacted for 17 hours as the temperature was raised to room temperature. The temperature of the flask was lowered to −30° C., TiCl$_4$ (3.02 ml, 1 M, 3.02 mmol) was slowly added thereto at −30° C. while stirring, and then the result was stirred for 6 hours as the temperature was raised to room temperature. After the reaction was complete, the solvent was removed under vacuum, and the residue was dissolved in toluene. The result was filtered and the filtrate was collected. Toluene was removed under vacuum to obtain a yellow brown compound (786.3 mg). The yield was 63.9%.

$^1$H NMR (C$_6$D$_6$): δ 0.12 (s, 3H, Ti—CH$_3$), 0.69 (s, 3H, Ti—CH$_3$), 1.61 (m, 2H, quin-CH$_2$), 1.67 (s, 3H, Cp-CH$_3$), 2.83 (m, 5H, Cp-CH$_3$), 4.45 (m, 2H, quin-CH$_2$), 6.82 (t, J=7.5

Hz, quin-CH), 6.91 (d, J=7.5 Hz, quin-CH), 6.96 (t, J=8 Hz, 1H, ph-CH), 7.11 (d, J=7 Hz, 1H, quin-CH), 7.18 (t, J=8 Hz, 1H, ph-CH), 7.22 (d, J=8 Hz, 1H, ph-CH), 7.83 (d, J=8 Hz, 1H, ph-CH) ppm.

Synthesis of Compound 2

Preparation of 7-(1,2-dimethyl-3H-benzo[b]cyclopenta[d]thiophen-3-yl)-2-methylindoline compound 2-methylindoline (1.64 g, 12.23 mmol) and diethylether (15 ml) were placed in a Schlenk flask. The Schlenk flask was immersed in a low temperature bath of −78° C. made of dry ice and acetone, and the mixture in the flask was stirred for 30 minutes. Subsequently, n-butyllithium (n-BuLi, 5.6 ml, 2.5 M, 13.95 mmol) was injected with a syringe under argon atmosphere, and dark yellow slurry was formed. Next, the generated butane gas was removed as the result was stirred for 3 hours while the temperature of the flask was raised to room temperature. The temperature was lowered once again by immersing the flask in a low temperature bath of −78° C., and carbon dioxide gas was introduced thereto. As the carbon dioxide gas was introduced, the yellow color gradually turned pale. The temperature was raised to room temperature while the carbon dioxide was removed by connecting the flask to a bubbler. The result gradually became white slurry. Subsequently, tetrahydrofuran (1.15 g, 15.90 mmol) and diethylether (5 ml) were added thereto in consecutive order. After the flask was immersed in a low temperature bath of −20° C., the mixture in the flask was stirred for 30 minutes, and tert-BuLi (9.72 ml, 1.7 M, 16.51 mmol) was added thereto. At this moment, the color of the reaction mixture turned to orange. The result was stirred for 4 hours while maintaining the temperature at −20° C. After lithium bromide (LiBr) (1.81 g, 20.80 mmol) and 1,2-dimethyl-1,2-dihydro-3H-cyclopenta-benzothiophen-3-one (1.72 g, 7.95 mmol) were dissolved in 16.30 ml of tetrahydrofuran in a syringe, the mixture was slowly introduced to the flask under argon atmosphere. The result was stirred for 1 hour at −20° C. in a low temperature reactor, and then stirred as the temperature was slowly raised to room temperature. Subsequently, 2.3 ml of water was added to the flask, ethyl acetate and hydrochloric acid (3 N, 30 ml) were added thereto, and the result was shaken for 5 minutes, and then the organic layer was extracted. Next, the organic layer was neutralized by adding a saturated aqueous sodium bicarbonate solution (30 ml) and TEA (1 ml), and then the organic layer was extracted once again. Anhydrous magnesium sulfate was added to this extracted organic layer in order to remove moisture, the result was filtered, the filtrate was collected, and the solvent was removed. The obtained filtrate was purified by column chromatography using an ethyl acetate and hexane (v/v, 1:20) solvent to obtain yellow solids. The yield was 49.0%.

$^1$H NMR ($C_6DCl_6$): 7.63-6.83 (m, 7H, Ar—H), 3.60 (br, 1H, N—H), 3.16-3.12 (m, 1H, N—CH), 2.89-2.41 (m, 2H, quin-CH$_2$), 1.93, 1.24 (s, 3H, Cp-CH$_3$), 0.95 (3H, quin-CH$_3$) ppm.

Preparation of [7-(1,2-dimethyl-3H-benzo[b]cyclopenta[d]thiophen-3-yl)-2-methylindolinyl]titanium dimethyl compound The 7-(1,2-dimethyl-3H-benzo[b]cyclopenta[d]thiophen-3-yl)-2-methylindoline (1.10 g, 3.32 mmol) prepared above was placed in a flask and was dissolved in 20 ml of diethyl-ether. The flask was immersed in a low temperature bath of −78° C., and the mixture in the flask was stirred for 30 minutes. Subsequently, MeLi (12.38 ml, 1.6 M, 19.81 mmol) was slowly added thereto. At this moment, the color of the reaction mixture turned to dark orange. The result was stirred overnight as the temperature was gradually raised to room temperature. Next, TiCl$_4$ (3.32 ml, 1 M, 3.32 mmol) was slowly added to the flask at −78° C. while stirring, and then the mixture was stirred for 5 hours as the temperature was raised to room temperature. After the reaction was complete, the solvent was removed under vacuum, and the residue was dissolved in toluene. The result was filtered and the filtrate was collected. Toluene was removed under vacuum to obtain a black compound (0.88 g). The yield was 65.3%. A cis-trans isomer (3:2) was identified according to $^1$H NMR analysis.

$^1$H NMR ($C_6D_6$) δ 7.80-6.78 (m, 7H, Ar—H), 4.97-4.92 (m, 1H, N—CH), 2.86-2.81 (m, 2H, quin-CH$_2$), 2.36, 1.71 (s, 3H, Cp-CH$_3$), 1.53 (d, 3H, quin-CH$_3$), 0.84, 0.21 (s, 3H, Ti—CH$_3$) ppm Synthesis of Compound 3

8-(1,2-dimethyl-1H-benzo[b]cyclopenta[d]thiophen-3-yl)-2-methyl-1,2,3,4-tetrahydroquinoline compound n-BuLi (14.9 mmol, 1.1 eq) was slowly added dropwise to a solution in which 2-methyl-1,2,3,4-tetrahydroquinoline (2 g, 13.6 mmol) was dissolved in 10 mL of ether at −40° C. The mixture was slowly warmed to room temperature, and then stirred for 4 hours at room temperature. After the temperature was lowered to −40° C. once again, CO$_2$ (g) was injected thereto, and the reaction was maintained for 0.5 hours at the low temperature. The result was slowly warmed, the remaining CO$_2$ (g) was removed through a bubbler. After THF (17.6 mmol, 1.4 ml) and t-BuLi (10.4 mmol, 1.3 eq) were injected thereto at −20° C., the result was low-temperature matured for 2 hours at −20° C. The ketone (1.9 g, 8.8 mmol) was dissolved in a 3 ml of diethyl ether and was slowly added dropwise thereto. After the result was stirred for 12 hours at room temperature, 10 mL of water was introduced thereto, and hydrochloric acid (2 N, 60 mL) was added thereto. The result was stirred for 2 minutes, the organic solvent was extracted, neutralized with an aqueous NaHCO$_3$ solution, and extracted once again, and the moisture was removed with MgSO$_4$. Yellow oil (1.83 g, 60% yield) was obtained through silica gel column.

$^1$H NMR ($C_6D_6$): δ 1.30 (s, 3H, CH$_3$), 1.35 (s, 3H, CH$_3$), 1.89~1.63 (m, 3H, Cp-H quinoline-CH$_2$), 2.62~2.60 (m, 2H, quinoline-CH$_2$), 2.61~2.59 (m, 2H, quinoline-NCH$_2$), 2.70~2.57 (d, 2H, quinoline-NCH$_2$), 3.15~3.07 (d, 2H, quinoline-NCH$_2$), 3.92 (broad, 1H, N—H), 6.79~6.76 (t, 1H, aromatic), 7.00~6.99 (m, 2H, aromatic), 7.30~7.23 (m, 2H, aromatic), 7.54~7.53 (m, 1H, aromatic), 7.62~7.60 (m, 1H, aromatic) ppm 8-(1,2-dimethyl-1H-benzo[b]cyclopenta[d]thiophen-3-yl)-2-methyl-1,2,3,4-tetrahydroquinoline-titanium dichloride compound n-BuLi (3.0 mmol, 2.1 eq) was slowly added dropwise to 8-(1,2-dimethyl-1H-benzo[b]cyclopenta[d]thiophen-3-yl)-2-methyl-1,2,3,4-tetrahydroquinoline (1.0 g, 2.89 mmol) at −20° C. The formation of yellow slurry was observed, and after the temperature was slowly raised to room temperature, the mixture was stirred for 12 hours at room temperature. After TiCl$_4$DME (806 mg, 2.89 mmol, 1.0 eq) was added dropwise thereto, the result was stirred for 12 hours at room temperature. The solvent was removed, and the result was extracted with toluene to obtain red solids (700 mg, 52% yield).

$^1$H NMR (C$_6$D$_6$): δ 1.46-1.467 (t, 2H, quinoline-N CH$_2$), 1.85 (s, 3H, Cp-CH$_3$), 1.79 (s, 3H, Cp-CH$_3$), 2.39 (s, 3H, Cp-CH$_3$), 2.37 (s, 3H, Cp-CH$_3$), 2.10-2.07 (t, 2H, quinoline-NCH$_2$), 5.22~5.20 (m, 1H, N—CH), 5.26~5.24 (m, 1H, N—CH), 6.89~6.87 (m, 2H, aromatic) 6.99~6.95 (m, 1H, aromatic), 7.19~7.08 (m, 2H, aromatic), 7.73~7.68 (m, 1H, aromatic) ppm Synthesis of Compound 4

Compound 4 was synthesized in the same manner as in the preparation example of Compound 1 synthesis method except that 1-methyl-1, 2-dihydro-3H-benzo[b]indeno[5,6-d]thiophen-3-one synthesized with reference to Organometallics 2002, 21, 2842 was used instead of 1,2-dimethyl-1H-benzo(b)cyclopenta(d)thiophen-3(2H)-one.

Synthesis of Compound 5

Compound 5 was synthesized in the same manner as in the preparation example of Compound 3 synthesis method except that 2-buthylquinoline synthesized with reference to Tetrahedron: Asymmetry 21 (2010) 1549 was used instead of 2-methyl-1,2,3,4-tetrahydroquinoline.

Preparation Example of Polymer

Examples 1 to 5 and Comparative Examples 1 and 2

After a hexane solvent (1.0 L) and 1-octene (1.1 M) were introduced to a 2 L autoclave reactor, the reactor was preheated to a temperature of 120° C. At the same time, the pressure of the reactor was filled with ethylene (35 bar) in advance. The compound (2.0 μmol) shown in the second row of the following Table 1 treated with a triisobutylaluminum compound and a dimethylanilinium tetrakis(pentafluorophenyl)borate cocatalyst (20 μmol) were placed in the reactor in consecutive order by adding high argon pressure (molar ratio of Al:Ti=10:1). Subsequently, the copolymerization reaction was progressed for 8 minutes. Next, the remaining ethylene gas was removed, and precipitation was induced by adding the polymer solution to excess ethanol. The precipitated polymer was washed 2 to 3 times each with ethanol and acetone, and then the physical properties of the polymer were measured after the polymer was dried in a vacuum oven for 12 hours or longer at 80° C.

Physical Property Evaluation (Weight, Activity, Melt Index, Melting Point, Density)

The melt index (MI) of the polymer was measured according to ASTM D-1238 (Condition E, 190° C., 2.16 Kg load). The melting point (Tm) of the polymer was obtained using a differential scanning calorimeter (DSC: 2920) manufactured by TA Instruments. In other words, after the temperature was raised to 200° C., the temperature was maintained for 5 minutes, and was lowered to 30° C., and then raised again, and the top of the DSC curve was measured as the melting point. Herein, the rate of the temperature increase and decrease was 10° C./min, and the melting point was obtained while the temperature was raised the second time. In addition, the density of the polymer was measured using a Mettler scale by preparing the sample in a sheet form having a thickness of 3 mm and a radius of 2 cm using a 180° C. press mold, and then cooling the sheet at 10° C./min.

The physical properties of the polymer prepared in Examples 1 to 5 and Comparative Examples 1 and 2 are shown in the following Table 1.

TABLE 1

| | Catalyst | Yield (kg/mmolTi) | MI2.16 | Density | Tc | Tm | Mw | MWD |
|---|---|---|---|---|---|---|---|---|
| Comparative Example 1 | CGC | 29 | 0.57 | 0.898 | 81.7 | 103.7 | 115540 | 5.40 |
| Comparative Example 2 | Compound A | 42 | 0.18 | 0.890 | (39.1), 69.4 | 87.0 | 155195 | 2.67 |
| Example 1 | Compound 1 | 47 | 0.65 | 0.879 | 56.6 | 72.7 | 126412 | 2.81 |
| Example 2 | Compound 2 | 20 | too low | 0.885 | 70.8 | 80.5 | 332217 | 2.00 |
| Example 3 | Compound 3 | 35 | 0.018 | 0.875 | 34.4, 71.3 | 53.8, 90.3 | 266933 | 2.63 |
| Example 4 | Compound 4 | 31 | n.d | n.d | (34.2) 71.1 | 82.9 | 67012 | 2.34 |
| Example 5 | Compound 5 | 34 | n.d | n.d | (broad) 100 | 112.0 | n.d | n.d |
| Example 6* | Compound 1 | 47 | 1.72 | 0.872 | 48.5 | 65.0 | 110069 | 2.56 |
| Example 7* | Compound 3 | 38 | 0.085 | 0.870 | 23.8, 69.5 | 46.4, 85.7 | 233155 | 2.45 |

Polymerization condition: hexane (1.0 L), ethylene (35 bar), 120° C., Cocat AB 10 equiv, 1-C8 1.1 (mol/L),
*: 1-C8 1.47 (mol/L), t = 8 min,
CGC: [Me$_2$Si(Me$_4$C$_5$)NtBu]TiMe$_2$ TABLE 1-continued
| Catalyst | Yield (kg/mmolTi) | MI2.16 | Density | Tc | Tm | Mw | MWD |
| --- | --- | --- | --- | --- | --- | --- | --- |
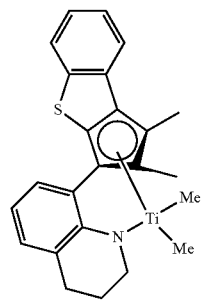
[Compound 1]
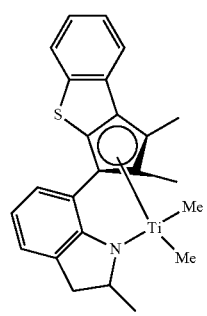
[Compound 2]
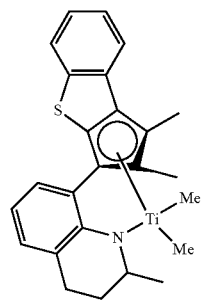
[Compound 3]
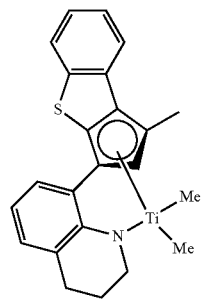
[Compound 4]

TABLE 1-continued

| Catalyst | Yield (kg/mmolTi) | MI2.16 | Density | Tc | Tm | Mw | MWD |
|---|---|---|---|---|---|---|---|

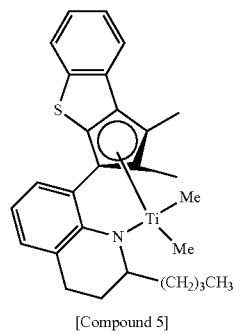

[Compound 5]

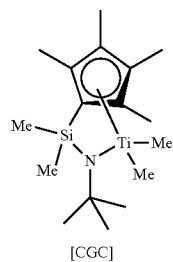

[CGC]

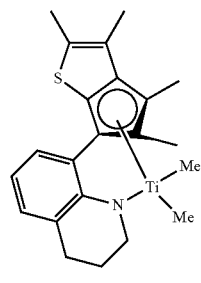

[Compound A]

MI2.16: Melt Index,
Tc: Crystallization Temperature,
Tm: Melting Temperature,
Mw: Weight Average Molecular Weight,
MWD: Molecular Weight Distribution (Weight Average Molecular Weight/Number Average Molecular Weight),
n.d: Non-detected As shown in Table 1, the compounds according to the present invention have excellent copolymerizability compared to the compounds in comparative examples thereby are capable of forming polymers with low density areas, and in the case of Compound 2 and Compound 3, polymers having a high molecular weight with a narrow MWD may be prepared.

The invention claimed is:

1. A transition metal compound of the following Chemical Formula 1:

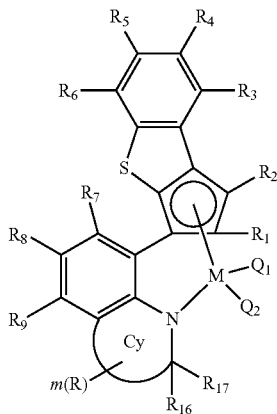

[Chemical Formula 1]

wherein, in Chemical Formula 1,

M is Ti, Hf or Zr;

$Q_1$ and $Q_2$ are the same as or different from each other, and each independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms;

$R_1$ to $R_6$ are the same as or different from each other, and each independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of group 14 metal substituted with hydrocarbyl having 1 to 20 carbon atoms; and $R_1$ and $R_2$ optionally bond to each other, or 2 or more of $R_3$ to $R_6$ optionally bond to each other to form an aliphatic ring having 5 to 20 carbon atoms; and the aliphatic ring is optionally substituted with halogen, alkyl having 1 to 20 carbon atoms, alkenyl having 2 to 20 carbon atoms, or aryl having 6 to 20 carbon atoms;

$R_7$ to $R_9$ are the same as or different from each other, and each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; and at least two of $R_7$ to $R_9$ optionally bond to each other to form an aliphatic ring having 5 to 20 carbon atoms; and the aliphatic ring is optionally substituted with halogen, alkyl having 1 to 20 carbon atoms, alkenyl having 2 to 20 carbon atoms, or aryl having 6 to 20 carbon atoms;

Cy is a 5-membered or 6-membered aliphatic ring;

R, $R_{16}$ and $R_{17}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; and m is an integer of 0 to 2 when Cy is a 5-membered aliphatic ring, and an integer of 0 to 4 when Cy is a 6-membered aliphatic ring.

2. The transition metal compound of claim 1, wherein the Chemical Formula 1 is represented by the following Chemical Formula 2 or 3:

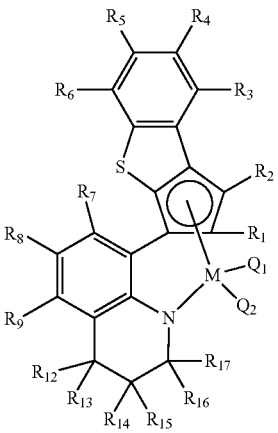

[Chemical Formula 3]

wherein, in Chemical Formula 2, $R_{12}$ to $R_{17}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; and the rest of the substituents are the same as those in Chemical Formula 1, and

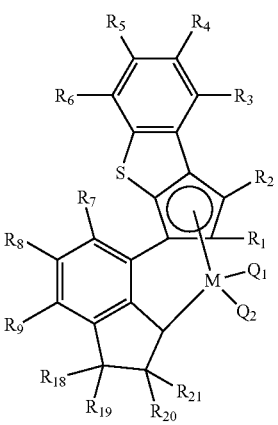

[Chemical Formula 3]

in Chemical Formula 3, $R_{18}$ to $R_{21}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; and the rest of the substituents are the same as those in Chemical Formula 1.

3. The transition metal compound of claim 1, wherein $R_1$ and $R_2$ are alkyl having 1 to 20 carbon atoms.

4. The transition metal compound of claim 1, wherein the compound represented by Chemical Formula 1 is represented by any one of the following chemical formulae:

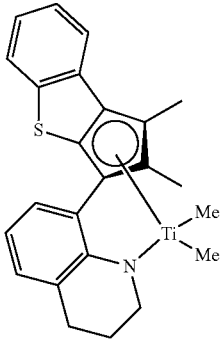
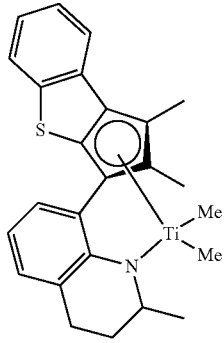
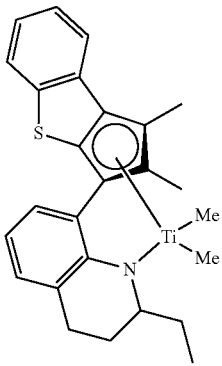
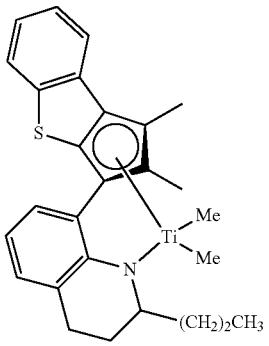
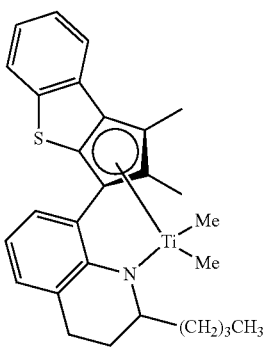
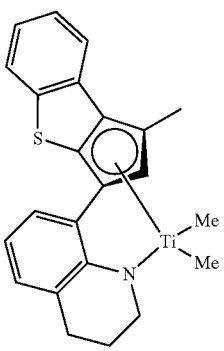
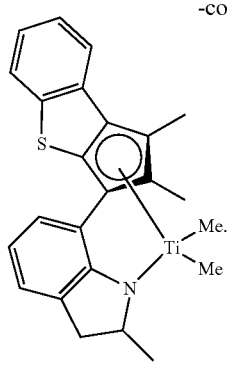

5. A catalytic composition comprising the transition metal compound of claim 1.

6. The catalytic composition of claim 5 further comprising one or more types of cocatalysts.

7. The catalytic composition of claim 6, wherein the cocatalyst includes one or more selected from among the following Chemical Formulae 10 to 12:

$$-[Al(R_{22})-O]_a-$$ [Chemical Formula 10]

wherein, in the formula, $R_{22}$s are each independently a halogen radical; a hydrocarbyl radical having 1 to 20 carbon atoms; or a hydrocarbyl radical having 1 to 20 carbon atoms substituted with halogen; and a is an integer of 2 or greater;

$$D(R_{22})_3$$ [Chemical Formula 11]

in the formula, D is aluminum or boron; $R_{22}$s are each independently the same as those defined above; and $$[L-H]^+[Z(A)_4]^- \text{ or } [L]^+[Z(A)_4]^-$$ [Chemical Formula 12]

in the formula, L is a neutral or cationic Lewis acid; H is a hydrogen atom; Z is a group 13 element; As are each independently aryl having 6 to 20 carbon atoms or alkyl having 1 to 20 carbon atoms in which one or more hydrogen atoms are optionally substituted with substituents; and the substituents are halogen, hydrocarbyl having 1 to 20 carbon atoms, alkoxy having 1 to 20 carbon atoms, or aryloxy having 6 to 20 carbon atoms.

8. The catalytic composition of claim 5 further comprising a reaction solvent.

9. A supported catalyst in which the catalytic composition of claim 5 is supported on a carrier.

10. A method for preparing a polymer using the catalytic composition of claim 5.

11. The method for preparing a polymer of claim 10, wherein the polymer is a polyolefin homopolymer or copolymer.

12. A method for preparing a polymer using the supported catalyst of claim 9.

13. The method for preparing a polymer of claim 12, wherein the polymer is a polyolefin homopolymer or copolymer.

* * * * *